(12) United States Patent
Schöler

(10) Patent No.: US 7,660,052 B2
(45) Date of Patent: Feb. 9, 2010

(54) OPTICAL BARREL ENCLOSING ROD LENSES

(75) Inventor: Uwe Schöler, Hoisdorf (DE)

(73) Assignee: Olympus Winter & IBE GmbH, Hamburg (DE)

( * ) Notice: Subject to any disclaimer, the term of this patent is extended or adjusted under 35 U.S.C. 154(b) by 27 days.

(21) Appl. No.: 11/850,321

(22) Filed: Sep. 5, 2007

(65) Prior Publication Data
US 2008/0062540 A1     Mar. 13, 2008

(30) Foreign Application Priority Data
Sep. 7, 2006  (DE) .................. 10 2006 041 920

(51) Int. Cl.
*G02B 7/02*     (2006.01)
*G02B 23/24*    (2006.01)
(52) U.S. Cl. .................. 359/811; 359/808; 359/435
(58) Field of Classification Search ............ 359/435, 359/808–813
See application file for complete search history.

(56) References Cited

U.S. PATENT DOCUMENTS

| 4,148,550 | A  | * | 4/1979  | MacAnally ............ 359/435 |
| 6,201,649 | B1 | * | 3/2001  | Rudischhauser et al. .... 359/808 |
| 6,301,043 | B1 | * | 10/2001 | Lei .................... 359/435 |
| 2008/0183042 | A1 | * | 7/2008 | Lederer et al. .......... 600/160 |

FOREIGN PATENT DOCUMENTS

| DE | 197 32 991 | 2/1999 |
| DE | 103 93 045 | 8/2005 |

* cited by examiner

*Primary Examiner*—Mohammed Hasan
(74) *Attorney, Agent, or Firm*—Rankin, Hall & Clark LLP

(57) ABSTRACT

An optical barrel (1) enclosing rod lenses (2) of a rigid endoscope optics, the rod lenses being contacted by the barrel in zones wherein an inwardly deforming, blade (4, 4') cut free by two associated cutouts (5, 5') in the barrel (1) is designed at each zone to make contact with rod lens (2).

6 Claims, 2 Drawing Sheets

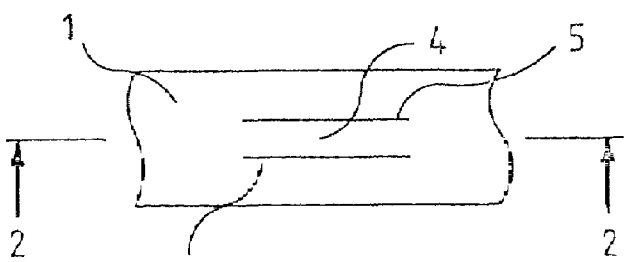
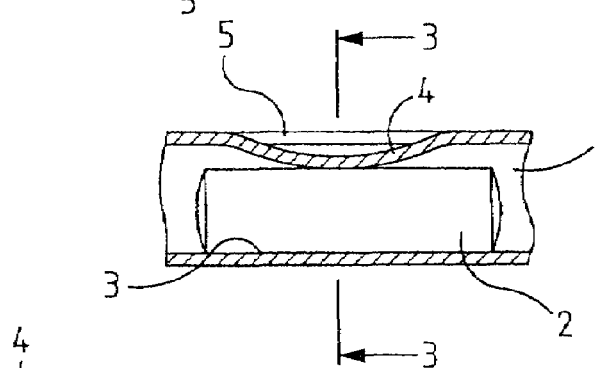
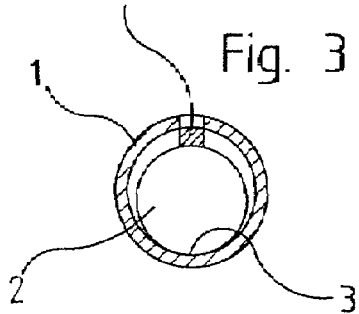
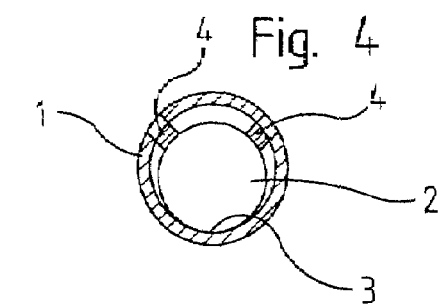
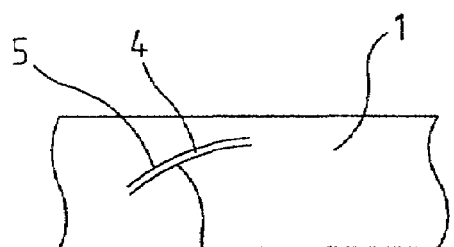
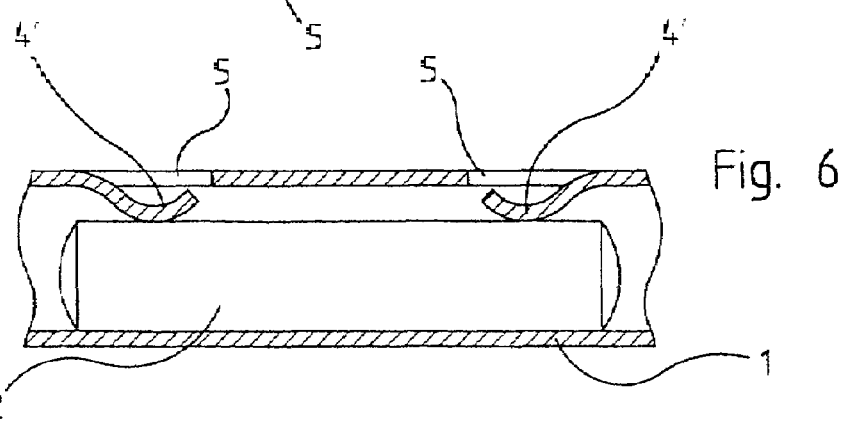

OPTICAL BARREL ENCLOSING ROD LENSES

BACKGROUND OF THE INVENTION

The present invention relates to an optical barrel, hereafter barrel, of the kind enclosing rod lenses of a rigid endoscope optics.

Rod lenses in endoscope optics serve as a relay system to transmit the image from a distal objective to a proximal ocular. A number of rod lenses are configured in a row and apart from each other. The endoscope optics is enclosed by a hermetically sealing cladding tube and includes a barrel within the cladding tube to keep the rod lenses accurately in place. The rod lenses must be sufficiently fixed in place within the barrel not to change their positions even when impacted in order to assure reproducible image transmission. The rod lens dimensions must be commensurately smaller than the barrel to allow axially displacing the lenses when the optical barrel is being assembled and, moreover, to preclude that slightly flexing the barrel should entail rod lens destruction.

To that end the rod lenses are only partly contacted by barrels of the above kind.

In a design of the above kind disclosed in German patent document DE 197 32 991 A1, rings are affixed to certain zones of the rod lenses, for instance at their ends, to brace the rod lenses against the barrel.

In a design of this kind disclosed in U.S. Pat. No. 4,148,550, the rod lenses are circular in cross-section though the barrel's cross-section is oval, as a result of which the rod lenses make contact along two lines with the barrel.

These known designs of the field being discussed entail elaborate manufacture and difficult assembly.

BRIEF SUMMARY OF THE INVENTION

The objective of the present invention is to create a system of the above kind which shall be manufactured more easily and allows easier lens rod installation.

In the design of the present invention, cutouts in the barrel define between them inwardly deformed, blades that are in contact with the rod lenses. These blades may be made very narrow, for instance being configured between parallel slits and, compared to the otherwise very rigid and unyielding tube may be easily depressed to a desired depth without thereby the surrounding barrel parts being deformed too. Said blades result in reliable spot retention at appropriated sites of the rod lens, assuring thereby the lens' stable and in particular impact-insensitive affixation. Such blades may be configured at different barrel sites in order to fix in place several sequentially arrayed rod lenses at one or several sites each, for instance each once at the lengthwise center of the rod lens or illustratively at both ends of the rod lens. Further, several blades might be arrayed apart from one another on the tube circumference to keep the rod lens at two circumferential sites and to force the rod lens into a clean three-spot support against the barrel.

The blades may be connected at both their ends to the barrel or preferably, they may be cut off along their length to be more easily deformed.

The barrel cutouts subtending the blades preferably may be configured in a grid array in a manner that the blades shall constitute a grid-like tube. In this manner, lengthwise or transverse blades may be depressed to keep the rod lenses in place.

The barrel may be made of a permanently deforming material, illustratively the blades being depressed toward the inserted rod lenses until contact is made. Advantageously however, the blades, like the remaining barrel, are designed to be resilient. The resilient blades may be permanently depressed prior to lens installation. In this case, the lenses will be moved axially through the resilient blades until reaching their desired assembly position.

The blades may be arrayed in a distributed manner in the barrel to contact the rod lenses, however they also may be advantageously configured in at least two rows where the blades of one row are staggered relative to the blades of the other row. In this manner, even very long blades allow densely arrayed axial contact spots and various lens configurations are made possible using a universally applicable barrel.

The present invention is shown in illustrative and schematic manner in the appended drawings.

BRIEF DESCRIPTION OF THE DRAWINGS

FIG. 1 is a sideview of a segment of the barrel comprising one resilient, blade, FIG. 2 is a cross-section along line 2-2 of FIG. 1, FIG. 3 is a cross-section along line 3-3 of FIG. 2, FIG. 4 is a cross-section of FIG. 3 of an embodiment variation comprising two circumferentially spaced, blades, FIG. 5 is similar to FIG. 1 except for an oblique blade, FIG. 6 is a cross-section corresponding to FIG. 2 comprising two axially apart blades loading a rod lens.

DETAILED DESCRIPTION OF THE INVENTION

Figure 7:
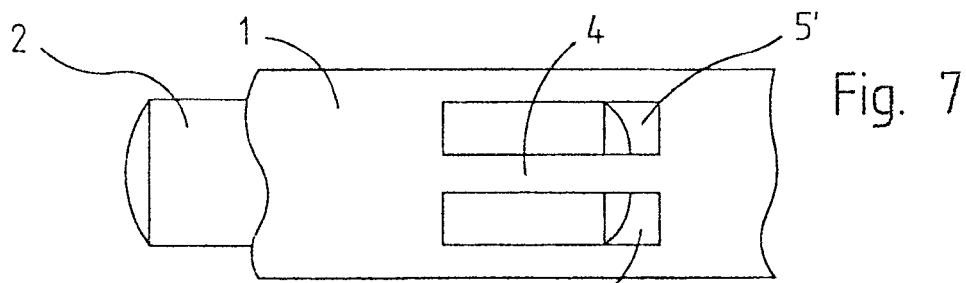
FIG. 7 is a side elevation corresponding to FIG. 1 indicating cutout zones next to the blades.

FIGS. 1-3 display a first embodiment mode of a barrel 1 of which only a small portion is shown, that for clarity shows an exaggerated play between the barrel 1 and an enclosed rod lens 2. This rod lens makes line-contact with the barrel 1 at the site 3, being kept in place at the opposite circumferential site by a blade 4 which is able to freely move inward between two cutouts 5 and illustratively is forced downward using an appropriate tool until making contact with the rod lens 2. For this purpose the material of the barrel 1 may be one retaining its new shape once deformed.

However, in a preferred embodiment of the present invention, the barrel is made of a spring material such as an appropriately elastic steel. The blade 4 is pre-shaped inward somewhat farther than indicated in FIGS. 2 and 3 and thereby may yield resiliently when the lens rod 2 is axially inserted as far as the shown assembly position.

To attain a three-point rest as seen in cross-section, two blades 4 may be used as shown in FIG. 4 which are circumferentially spaced apart and which jointly with the linear contact at the site 3 result in a three-point rest.

As shown in FIGS. 1-4, the blades 4 are aligned parallel to the axis of the barrel 1. However, and illustratively, said blades may also be configured transversely to said axis or for instance be oblique as indicated in an embodiment shown in FIG. 5.

FIG. 6 is a cross-section of an embodiment variation substantially corresponding to that of FIGS. 1-3. However two blades 4' are mounted axially apart to keep a rod lens 2 in place in the barrel 1 in such a manner that they touch the rod lens 2 near its ends to keep it in place.

In the embodiment mode of FIGS. 1-3, the blades 4 are connected at both ends to the remainder of the barrel 1. In the embodiment mode of FIG. 6, however, the blades 4' are severed from the barrel at one site of their length, that is, they are connected only at one end to the barrel while being free at the other. This feature allows improved deformation and, in the case of spring-elastic materials, more compliant resilience. Preferably and as shown in FIG. 6, the resilient, blades 4' curve upward again at their ends, resting with a well gliding rounded part against the rod lens 2.

FIG. 7 shows an embodiment variation substantially corresponding to the embodiment of FIG. 1. In this design, however, the blade 4 no longer is bounded at its sides by the cutouts 5 of the embodiment mode of FIG. 1, instead it is bounded by the comparatively large cutouts 5'. The flexure and spring properties of the blade 4 are substantially the same as in the embodiment mode of FIG. 1. The cutouts 5' allow access to the rod lens(es) 2, for instance, for purposes of adjustment.

In the embodiment modes of FIGS. 1-7, the blades 4 or 4' should be configured so as to recur along the length of the barrel 1 at those sites where the consecutive rod lenses 2 of a relay lens system must be configured in their final assembled position.

Figure 8:
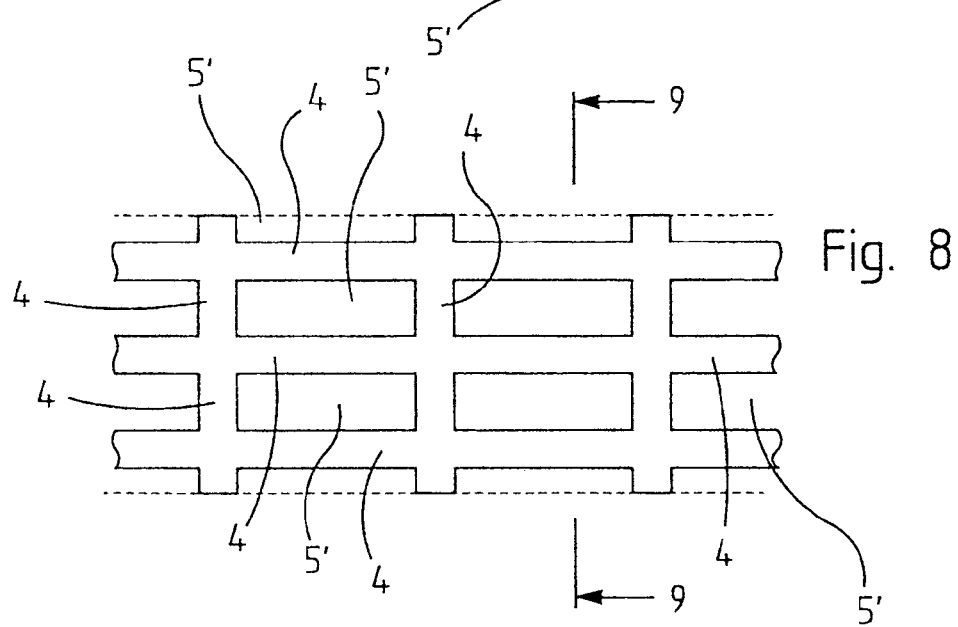
FIG. 8 is a side elevation corresponding to FIG. 1 fitted with a grid barrel.
Figure 9:
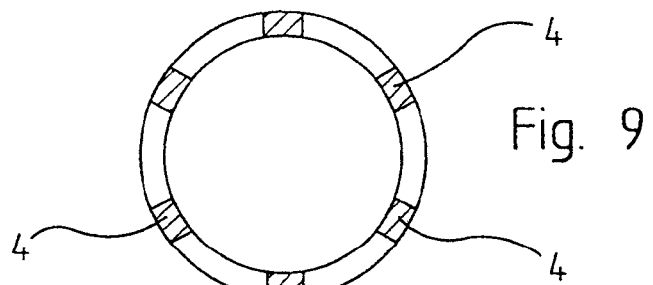
FIG. 9 is a cross-section along line 9-9 of FIG. 8.

In a further development of the embodiment mode of FIG. 7, the pattern of cutouts 5' may be regularly repeated in the form of a grid pattern, whereby the barrel 1 is constituted as a grid barrel of which the blades 4 are joined longitudinally and transversely at their intersections. Any arbitrary longitudinal or transverse blade 4 may be depressed to keep in place a rod lens (not shown in FIGS. 8 and 9) situated underneath.

Figure 10:
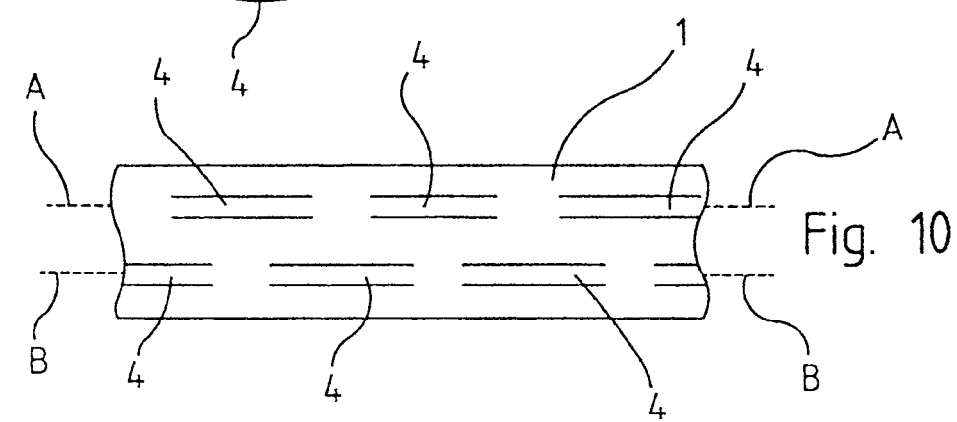
FIG. 10 is a side elevation corresponding to FIG. 1 of another embodiment mode of the present invention.

FIG. 10 shows a further embodiment mode of a barrel 1 of which the blades 4 correspond to the embodiment mode of FIG. 1 and are mutually configured one behind the other in two parallel rows A and B. As shown by FIG. 10, the blades are longitudinally staggered in each row A and B. From this results the possibility to hold the lenses in positions following one another very closely in the direction of the barrel 1, the holding can be achieved e.g. according to FIG. 2 with blades 4 from one of the two rows A, B. In this manner, very short lenses too may be kept in position very reliably and hence the barrel of FIG. 10 may be used universally for the various sets of lenses. Besides the two rows A and B shown in FIG. 10, more rows of blades 4 may also be used.

In FIG. 10, the two rows A and B are fitted with blades 4 running in the direction of the rows. However, as shown by FIG. 5 for instance, the blades also my run obliquely to said rows.

The invention claimed is:

1. An optical barrel enclosing rod lenses of a rigid endoscope optics, the rod lenses being contacted by the barrel in zones, said barrel comprising a first cross-sectional shape outside of said zones and a second cross-sectional shape inside of said zones, said second cross-sectional shape comprising portions deformed inwardly with respect to said first cross-sectional shape, said portions being defined by blades cut out from said barrel.

2. Barrel as claimed in claim 1, wherein the cutouts that define the blades are parallel slits.

3. Barrel as claimed in claim 1, wherein the blades are cut off at one site of their length.

4. Barrel as claimed in claim 1, wherein the cutouts that define the blades are configured in a manner that the blades constitute a grid barrel.

5. Barrel as claimed in claim 1, wherein the barrel is made of a spring-elastic material.

6. An optical barrel enclosing rod lenses of a rigid endoscope optics, the rod lenses being contacted by the barrel in zones wherein an inwardly deform blade cut free between two cutouts in the barrel is designed at each zone to make contact with the rod lens and wherein several blades are arranged one behind the other in at least two rows (A, B) parallel to the axis of the barrel with an offset of the blades of one row (A) with respect to those of the other row (B).

* * * * *